United States Patent
Weinberg

(10) Patent No.: US 9,757,174 B2
(45) Date of Patent: Sep. 12, 2017

(54) IMPLANT, A METHOD FOR PRODUCTION THEREOF AND USE THEREOF

(71) Applicant: Annelie-Martina Weinberg, Schüttorf (DE)

(72) Inventor: Annelie-Martina Weinberg, Schüttorf (DE)

(*) Notice: Subject to any disclaimer, the term of this patent is extended or adjusted under 35 U.S.C. 154(b) by 0 days.

(21) Appl. No.: 15/026,966

(22) PCT Filed: Oct. 3, 2014

(86) PCT No.: PCT/EP2014/071255
§ 371 (c)(1),
(2) Date: Apr. 2, 2016

(87) PCT Pub. No.: WO2015/049379
PCT Pub. Date: Apr. 9, 2015

(65) Prior Publication Data
US 2016/0256208 A1   Sep. 8, 2016

(30) Foreign Application Priority Data
Oct. 3, 2013 (EP) .................................... 13187287

(51) Int. Cl.
| | |
|---|---|
| A61B 17/86 | (2006.01) |
| C22C 23/00 | (2006.01) |
| C22C 23/04 | (2006.01) |
| C22F 1/06 | (2006.01) |
| A61B 17/72 | (2006.01) |
| A61L 27/04 | (2006.01) |
| A61L 27/58 | (2006.01) |
| A61L 31/02 | (2006.01) |
| A61L 31/14 | (2006.01) |
| A61B 17/84 | (2006.01) |

(52) U.S. Cl.
CPC ............ A61B 17/866 (2013.01); A61B 17/72 (2013.01); A61B 17/842 (2013.01); A61L 27/047 (2013.01); A61L 27/58 (2013.01); A61L 31/022 (2013.01); A61L 31/148 (2013.01); C22C 23/00 (2013.01); C22C 23/04 (2013.01); C22F 1/06 (2013.01); A61B 17/84 (2013.01); A61L 2430/02 (2013.01)

(58) Field of Classification Search
CPC .... A61B 17/866; A61L 27/306; A61L 27/047
See application file for complete search history.

(56) References Cited

FOREIGN PATENT DOCUMENTS

| | | |
|---|---|---|
| CN | 1792383 A | 6/2006 |
| DE | 102009002709 A1 | 4/2010 |
| EP | 1840235 A1 | 10/2007 |
| EP | 2511390 A2 | 10/2012 |
| WO | 2009148515 A1 | 12/2009 |
| WO | 2013052791 A2 | 4/2013 |
| WO | 2013107644 A1 | 7/2013 |
| WO | 2014001321 A1 | 1/2014 |
| WO | 2014159328 A1 | 10/2014 |

OTHER PUBLICATIONS

Saeed Farahany, et al., "In-Situ Thermal Analysis and Macroscopical Characterization of Mg—xCa and Mg-0.5Ca—xZn Alloy Systems," Thermochimica Acta, Nov. 2, 2011, pp. 180-189, 527 (2012) Elsevier B.V.
Erlin Zhang, et al., "Microstructure, Mechanical Properties and Bio-Corrosion Properties of Mg—Zn—Mn—Ca Alloy for Biomedical Application," Materials Science and Engineering A, pp. 111-118, 497 (2008) Elsevier B.V.
M. Bamberger, et al., "Trends in the Development of New Mg Alloys," Annu. Rev. Mater. Res., Apr. 18, 2008, pp. 505-533, vol. 38, University of Vienna.
Tsutomu Sugiura, DDS, et al., "A Comparative Evaluation of Osteosynthesis With Lag Screws, Miniplates, or Kirschner Wires for Mandibular Condylar Process Fractures," J. Oral Maxillofac. Surg., 2001, pp. 1161-1168, vol. 59.
Xuesong Li, et al., "Microstructure, Mechanical Properties and Corrosion Behavior of Mg—1Zn—0.5Ca Alloy," Advanced Materials Research vols. 311-313 (2011) pp. 1735-1740, Trans Tech Publications, Switzerland.
Baoping Zhang, et al., "Mechanical Properties, Degradation Performance and Cytotoxicity of Mg—Zn—Ca Biomedical Alloys With Different Compositions," Materials Science and Engineering C, Jul. 30, 2011, pp. 1667-1673, vol. 31, Elsevier B.V.
K. Oh-Ishi, et al., "Age-Hardening Response of Mg-0.3 at.%Ca Alloys With Different Zn Contents," Materials Science and Engineering A, (2009) pp. 177-184, vol. 526, Elsevier B.V.
J.C. Oh, et al., "TEM and 3DAP Characterization of an Age-Hardened Mg—Ca—Zn Alloy," Scripta Materialia, Jun. 28, 2005, pp. 675-679, vol. 53, Elsevier Ltd.
Horst E. Friedrich, et al., "Magnesium Technology," 2006, pp. 310-313, Springer, Germany.

*Primary Examiner* — Andrew Yang

(57) ABSTRACT

An implant, a method for production thereof, and use thereof for growing patients are disclosed, containing a Mg—Zn—Ca-based alloy. In order to meet extremely strict requirements with regard to compatibility, chemical resistance, and mechanical strength, it is proposed that the alloy contain 0.1 to 0.6 wt % zinc (Zn), 0.2 to 0.6 wt % calcium (Ca), and a remainder of magnesium (Mg), as well as impurities that are an inevitable part of the manufacturing process, which each total no more than 0.01 wt % and altogether total at most 0.1 wt %, with the quotient of the percentages by weight of Zn and Ca being less than or equal to 1.

12 Claims, No Drawings

IMPLANT, A METHOD FOR PRODUCTION THEREOF AND USE THEREOF

FIELD OF THE INVENTION

The invention relates to an implant for growing patients, with a Mg—Zn—Ca-based alloy.

BACKGROUND OF THE INVENTION

The prior art has disclosed biodegradable implants (DE102009002709A1) whose material is composed of a magnesium alloy. Among the magnesium alloys, Mg—Zn—Ca-based alloys are also known, whose main alloying elements are biocompatible with the human organism. It is thus possible to avoid occurrences of irritation in regions surrounding such an implant. In addition, this biocompatibility of the main alloying elements also opens up the possibility of using implants—in particular nails for osteosynthesis—in pediatrics and adolescent medicine since the dissolving main alloying elements can be absorbed and utilized by the organism of the growing person. For strength reasons, the known Mg—Zn—Ca-based nails also have a comparatively high Zn content; this results in a reduced corrosion resistance of the nail, though. Secondary alloying elements, in particular rare earths, can in turn increase the corrosion resistance of the nail, but they reduce its biocompatibility, thus making nails that are constructed in this way risky to use, particularly in pediatrics and adolescent medicine.

SUMMARY OF THE INVENTION

The object of the invention, therefore, is to improve a Mg—Zn—Ca-based implant of the type described at the beginning so that it has a high strength and also meets the highest demands with regard to its biocompatibility with the human organism, particularly of a child or a patient that is growing.

The invention attains the stated object with regard to the implant in that the alloy contains 0.1 to 0.6 wt % zinc (Zn), 0.2 to 0.6 wt % calcium (Ca), and a remainder of magnesium (Mg), as well as impurities that are an inevitable part of the manufacturing process, which each total no more than 0.01 wt % and altogether total, at most 0.1 wt %, with the quotient of the percentages by weight of Zn and Ca being less than or equal to 1.

If the alloy has 0.1 to 0.6 wt % zinc (Zn), then as a result of this reduced Zn content, an increased corrosion resistance of the implant can be expected. On the other hand, however, the reduced Zn content means that a reduced solid solution hardening can be expected. The invention can reduce this disadvantage of the thus-reduced strength in that the alloy contains 0.2 to 0.6 wt % calcium (Ca) and the quotient of the percentages by weight of Zn and Ca is less than or equal to 1 [((wt % Zn)/(wt % Ca))≤1]. Specifically, it has turned out that with the aid of this limit in the composition of the alloy, it is possible to precipitate chiefly a (Mg,Zn)2Ca phase (intermetallic phase). The formation of other intermetallic phases such as MgZn2 and Mg6Zn3Ca2 can be advantageously suppressed, which on the one hand, can be an advantage with regard to a lower degradation speed of the implant. In addition, the (Mg,Zn)2Ca particles in the alloy according to the invention act as obstacles to displacements, i.e. a particle hardening occurs, which can contribute to a significant strength increase of the alloy. The intermetallic (Mg,Zn)2Ca precipitation, however, also advantageously inhibits the grain growth, which can significantly improve the strength and ductility of the implant. Since this (Mg,Zn)2Ca phase is also baser than the Mg matrix, which is comparatively base as is, (Mg,Zn)2Ca phases that "pin" the grain boundary do not function as cathodic sites and as a result, do not interfere with a uniform corrosion attack. The latter also avoids a particularly disadvantageous point corrosion, which is partly responsible for the creation of local stability problems in the implant and thus for breakage. The medical implant according to the invention can thus also provide a mechanical strength that decreases uniformly over the course of its biodegradation in order to thus correspond to the desired therapy or use in the organism. As a result, such an implant can be particularly suitable for osteosynthesis. Because of the comparatively high stability and resistance to corrosion and mechanical stresses, it can also be unnecessary to use additional alloying elements such as rare earths. It is therefore sufficient if in addition to the alloying elements Zn and Ca, the implant contains a remainder of magnesium (Mg) as well as impurities that are an inevitable part of the manufacturing process, which each total no more than 0.01 wt % and altogether total at most 0.1 wt %. The implant according to the invention is thus composed almost entirely of biocompatible elements. Considering the above-mentioned advantages, this can be particularly suitable for patients who are growing.

In general, it should be noted that the implant for the osteosynthesis can be a Krischner wire, a Herbert screw, a medullary nail, or the like. Preferably, the implant is a nail for elastically stable medullary splinting (ESIN).

The alloy can meet particularly high demands on stability and resistance to corrosion as well as mechanical load-bearing capacity if with regard to intermetallic phases, its Mg matrix contains essentially—i.e. more than 50%—(Mg,Zn)2Ca precipitation phases.

The above can be further improved if the Mg matrix of the alloy contains exclusively (Mg,Zn)2Ca precipitation phases.

Another object of the invention is to simplify a method for producing an implant —and to nevertheless reproducibly ensure a comparatively high chemical resistance and mechanical strength. Moreover, it should also be possible to carry out the method in a comparatively inexpensive way.

The invention attains the stated object with regard to the method for producing an implant for growing patients in that its alloy is kept at a temperature in the range from 200 to 400 degrees Celsius in order to develop (Mg,Zn)2Ca precipitation phases.

If its alloy is kept at a temperature in the range from 200 to 400 degrees Celsius in order to develop (Mg,Zn)2Ca precipitation phases, then the growth of (Mg,Zn)2Ca precipitation phases can be selectively influenced so that particularly fine-grained (Mg,Zn)2Ca precipitation phases can be produced. It is thus possible to reproducibly manufacture a medical implant in an easy-to-manage way, with a high mechanical strength. In addition, the method according to the invention can also provide for (Mg,Zn)2Ca precipitation phases that are uniformly distributed in the Mg matrix in order to ensure a uniform biodegradation of the implant. Depending on the duration of this temperature treatment, the mechanical strength and chemical resistance of the alloy can thus be designed in accordance with the desired therapy or the use in the organism. This can be advantageous particularly in a medical implant for osteosynthesis, primarily also in pediatrics and adolescent medicine, which implant is for example a Krischner wire, a Herbert screw, a medullary nail, a nail for elastically stable medullary splinting (ESIN), or the like. In general, it should be noted that this temperature treatment can take place in a wide variety of method steps for producing the implant, for example before a hot forming of the blank, during the hot forming (e.g. through extrusion, forging, rolling, or the like), and/or during a heat treatment (e.g. through annealing, artificial aging, or the like). The step taken according to the invention is therefore particularly user-friendly and simplifies the method considerably.

If the alloy is kept at a temperature in the range from 200 to 275 degrees Celsius, then it is possible to further increase the formation of (Mg,Zn)2Ca precipitation phases in this sub-range.

As mentioned above, the alloy can be stimulated for the preferred formation of (Mg,Zn)2Ca precipitation phases if the alloy is kept at the temperature before the hot forming.

Preferably, before and during the hot forming, the alloy is kept at the temperature in order to form (Mg,Zn)2Ca precipitation phases so as to combine this heat treatment with the forming and to thus carry out the method more quickly and economically. A hot forming can conceivably be in the form of extrusion, forging, rolling, or the like. For example, a forging of the implant blank a can be particularly well-suited to optimizing the mechanical and chemical properties of the implant. After its hot forming, the implant can be subjected to a finishing treatment, for example a material-removing machining.

It is also conceivable to obtain the (Mg,Zn)2Ca precipitation phases by keeping the alloy at the temperature for the formation of (Mg,Zn)2Ca precipitation phases during the artificial aging.

The invention can be particularly advantageous when used as a material for producing an implant for growing patients and for use in osteosynthesis if it is a Mg—Zn—Ca-based alloy containing 0.1 to 0.6 wt % zinc (Zn), 0.2 to 0.6 wt % calcium (Ca), and a remainder of magnesium (Mg), as well as impurities that are an inevitable part of the manufacturing process, which each total no more than 0.01 wt % and altogether total, at most 0.1 wt %, with the quotient of the percentages by weight of Zn and Ca being less than or equal to 1 [((wt % Zn)/(wt % Ca))≤1].

In particular, the material can be particularly suitable for use in a Krischner wire, a Herbert screw, a medullary nail, and/or a nail for elastically stable medullary splinting (ESIN).

DETAILED DESCRIPTION OF THE PREFERRED EMBODIMENTS

To document the achieved effects, medical implants in the form of nails were produced from different Mg—Zn—Ca-based alloys. The compositions of the alloys tested are specified in Table 1.

TABLE 1

Overview of the nails

| Nail no. | Composition |
|---|---|
| 1 | MgZn1, Ca0, 25Mn0, 15Y2 |
| 2 | MgZn5, Ca0, 25Mn0, 15 |
| 3 | MgZn0, 4Ca0, 4 |

Nail no. 1 in Table 1 is made of a known magnesium alloy using rare earths Y as an alloying element. Nail no. 2 in Table 1, which is likewise known from the prior art, does not use rare earths as alloying elements, but requires an elevated percentage of Zn in order to achieve the desired strength, which reduces the chemical resistance (corrosion resistance) of the nail. Nail no. 3, whose composition is indicated by way of example in Table 1, contains the magnesium alloy according to the invention. With 0.4 wt % Zn, nail no. 3 lies in the claimed range of from 0.1 to 0.6 wt % Zn and with 0.4 wt % Ca, it lies in the claimed range of from 0.2 to 0.6 wt % Ca. The quotient of the weight percentages of Zn and Ca (wt % Zn divided by wt % Ca) is 1 and is therefore also less than or equal to 1, as required according to the invention. This nail no. 3 was produced from a cooled, extruded blank with subsequent material-removing machining. The extrusion was carried out within the temperature limits of 200 to 400° C.

The above-mentioned nails were tested for their chemical resistances and mechanical strengths. To accomplish this, the tensile strength Rm, the yield strength Rp0,2, and the flexural strength A5 were determined in the tensile test. In addition, the degradation in SBF (simulated bodily fluid) was measured. The measurement values obtained are summarized in Table 2.

TABLE 2

Measurement results of the tested nails

| Nail no. | $R_{p0,2}$ [MPa] | $R_m$ [MPa] | $A_5$ | SBF [mm/year] |
|---|---|---|---|---|
| 1 | 150 | 250 | 20 | 0.5 |
| 2 | 210 | 295 | 18 | 4 |
| 3 | 200 | 250 | 22 | 0.25 |

As can be inferred from Table 2, the low zinc content of nail no. 3 compared to nail no. 2 does not result in any disadvantages in the mechanical strength, but does as a result enjoy the considerable benefit of an increased chemical resistance of at most 0.25 mm/year of degradation. This is even lower than the degradation measured in nail no. 1, whose alloy disadvantageously contains rare earths.

A stable, biodegradable implant is thus achieved, which is particularly well-suited for pediatrics and adolescent medicine and for growing patients in general. This is assured since no rare earths are used, the alloying components are thus biocompatible, and they can thus be used by the growing organism—but it is also nevertheless possible to provide high mechanical strength and chemical resistance.

The invention claimed is:

1. An implant for growing patients containing a Mg—Zn—Ca-based alloy, the alloy consisting essentially of:
   0.1 to 0.6 wt % zinc (Zn),
   0.2 to 0.6 wt % calcium (Ca), and a remainder of magnesium (Mg), as well as impurities that are an inevitable part of a manufacturing process, which each total no more than 0.01 wt % and altogether total at most 0.1 wt %, with a quotient of the percentages by weight of Zn and Ca being less than or equal to 1.

2. The implant according to claim 1, wherein, with regard to intermetallic phases, the Mg matrix of the alloy contains essentially (Mg,Zn)2Ca precipitation phases.

3. The implant according to claim 2, wherein the Mg matrix of the alloy contains exclusively (Mg,Zn)2Ca precipitation phases.

4. The implant according to claim 1, wherein the implant is used for osteosynthesis.

5. A method for producing the implant for growing patients according to claim 1, comprising keeping the alloy at a temperature in a range from 200 to 400 degrees Celsius in order to produce (Mg,Zn)2Ca precipitation phases.

6. The method according to claim 5, comprising keeping the alloy at a temperature in the range from 200 to 275 degrees Celsius in order to produce (Mg,Zn)2Ca precipitation phases.

7. The method according to claim 5, wherein, before hot for the alloy is kept at a temperature in order to produce (Mg,Zn)2Ca precipitation phases.

8. The method according to claim 5, wherein, during hot forming, the alloy is kept at a temperature in order to produce (Mg,Zn)2Ca precipitation phases.

9. The method according to claim 5, wherein, during artificial aging, the alloy is kept at the temperature for the formation of (Mg,Zn)2Ca precipitation phases.

10. The method according to claim 5, further comprising producing an implant for osteosynthesis.

11. A method of using the implant according to claim 1, comprising using the alloy as a material for producing the implant for growing patients for use in osteosynthesis.

12. The method according to claim 11, comprising using the implant as a Krischner wire, a Herbert screw, a medullary nail, and/or a nail for elastically stable medullary splinting (ESIN), or the like.

* * * * *

UNITED STATES PATENT AND TRADEMARK OFFICE
CERTIFICATE OF CORRECTION

Page 1 of 1

PATENT NO. : 9,757,174 B2
APPLICATION NO. : 15/026966
DATED : September 12, 2017
INVENTOR(S) : Annelie-Martina Weinberg It is certified that error appears in the above-identified patent and that said Letters Patent is hereby corrected as shown below:

In the Claims

Column 5, Claim 7, Line 2, replace "for" with --forming,--.

Signed and Sealed this
Seventh Day of November, 2017

Joseph Matal
*Performing the Functions and Duties of the
Under Secretary of Commerce for Intellectual Property and
Director of the United States Patent and Trademark Office*